United States Patent [19]

Kaibel et al.

[11] 4,383,893
[45] May 17, 1983

[54] DISTILLATIVE SEPARATION OF LIQUID MIXTURES CONTAINING ALIPHATIC ALCOHOLS

[75] Inventors: Gerd Kaibel, Lampertheim; Horst Hartmann, Boehl-Iggelheim; Waldhelm Hochstein, Freinsheim; Franz-Josef Mueller, Wachenheim, all of Fed. Rep. of Germany

[73] Assignee: BASF Aktiengesellschaft, Ludwigshafen, Fed. Rep. of Germany

[21] Appl. No.: 255,429

[22] Filed: Apr. 20, 1981

[30] Foreign Application Priority Data

May 23, 1980 [DE] Fed. Rep. of Germany ........ 3019766

[51] Int. Cl.$^3$ ............................................. B01D 3/34
[52] U.S. Cl. ........................................ 203/35; 203/41; 203/98; 568/913

[58] Field of Search ..................... 568/913; 203/51, 54, 203/61, 62, 18, 19, 56, 63, 66, 28, 35, 34, 41, 39, 98

[56] References Cited

U.S. PATENT DOCUMENTS 3,268,572 8/1966 Knörr et al. ........................... 203/63
3,404,175 10/1968 Mercier .................................. 203/61

Primary Examiner—Frank Sever
Attorney, Agent, or Firm—John H. Shurtleff

[57] ABSTRACT

Liquid mixtures containing aliphatic alcohols are separated, by distillation, into a higher-boiling alcohol-containing fraction and a lower-boiling fraction containing the other liquids, by carrying out the fractionation in the presence of water and of an alkanal and, over about ¾ of the column height, in the presence of a non-volatile or only slightly volatile acid.

6 Claims, 1 Drawing Figure me = methanol
me-ac = methyl acetate
H$_2$O/H$^+$ = aqueous acid
ald = acetaldehyde

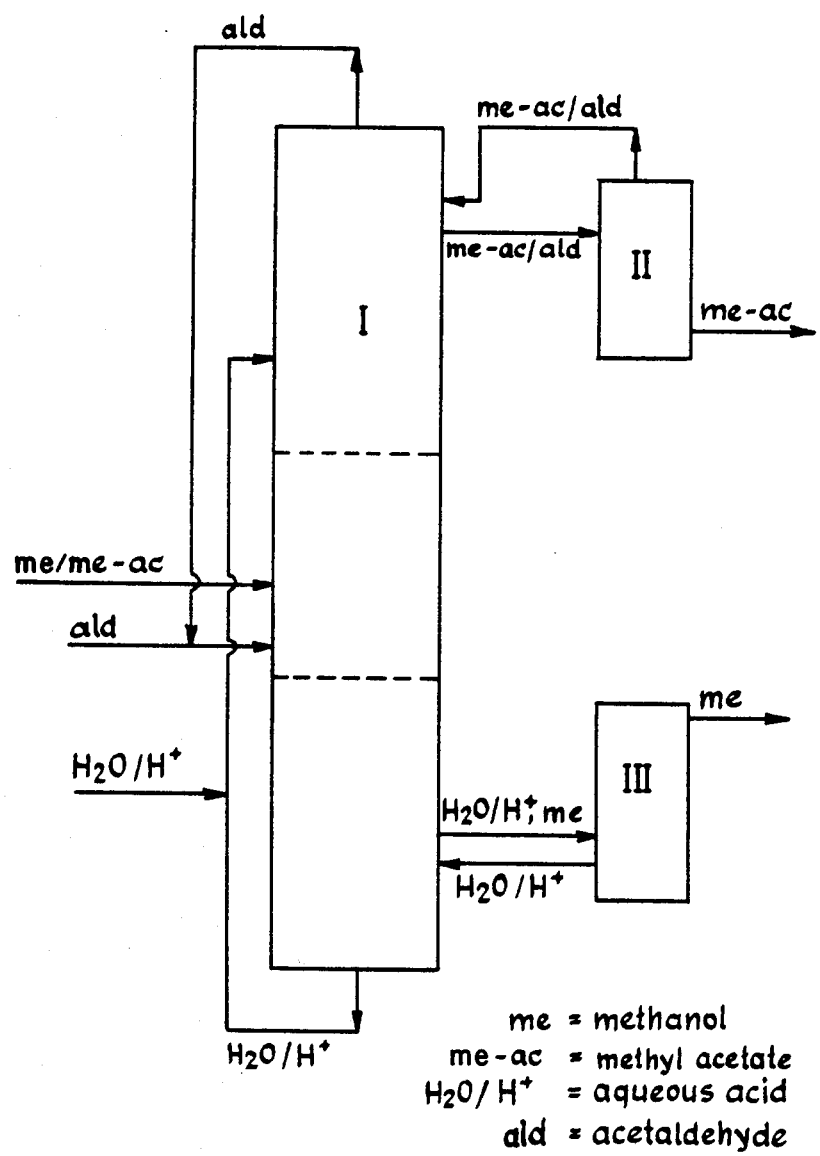

DISTILLATIVE SEPARATION OF LIQUID MIXTURES CONTAINING ALIPHATIC ALCOHOLS

The present invention relates to a novel process for the distillative separation of liquid mixtures, containing aliphatic alcohols, into a higher-boiling alcohol-containing fraction and a lower-boiling fraction containing the other liquids.

In the simplest case, the problem concerns the separation of a two-component mixture, namely a mixture of an alcohol and of a lower-boiling substance. Of course, there are no difficulties if the two components have substantially different boiling points or if they do not form an azeotrope. However, if these preconditions do not apply, so that a normal fractionation is not successful, it is necessary to employ technically complicated methods, for example fractionation under alternately increased and reduced pressure, extractive processes or distillation in the presence of an auxiliary. These processes have the further disadvantage that they are only applicable in quite specific cases. If the composition of the mixture changes, or if new types of mixtures have to be separated, it is in most cases also necessary to find a new method.

What is true of the two-component system is in general also true of any alcohol-containing mixtures, except that an alcohol-containing fraction, and a lower-boiling alcohol-free fraction, are obtained, and at least one of these fractions consists of more than one component, so that it may be necessary subsequently to carry out additional separation processes.

It is an object of the present invention to provide a method for separating liquid mixtures, containing aliphatic alcohols, into an alcohol-containing fraction and a lower-boiling fraction of the other components, and in particular to do so by a generally applicable process in cases where simple fractionation is unsatisfactory.

We have found that this object is achieved and that liquid mixtures containing aliphatic alcohols can be separated by distillation, in a fractionating column, into an alcohol-containing fraction and a lower-boiling fraction of the other components, if the fractionation is carried out in the presence of water and of an alkanal and, over about ¾ of the column height, in the presence of a non-volatile or only slightly volatile acid.

This process is based on the principle that in the middle zone of the column the alcohol is transiently bonded to the alkanal to form a higher-boiling acetal or hemiacetal, so that only the substances which are more volatile than the alcohol can pass into the upper zone of the column, where they can subsequently be taken off at the top. In the lower zone of the column, the acetal or hemiacetal is cleaved again, so that there a mixture of the alcohol, water, the alkanal and any additional higher-boiling components are obtained.

If the alkanal v is more volatile than the alcohol, some of the alkanal passes into the top product, from which it can be separated in a further process step. It is possible to select the alkanal so that this separation presents no problems.

If, on the other hand, the alkanal is less volatile than the top product, it remains in the aqueous bottom phase, which as a rule can be separated conventionally into its components.

The process will be illustrated, with the aid of the drawing, in relation to the separation of methyl acetate and methanol by means of a lower-boiling alkanal, this being a case which is typical of the invention and is of particular industrial importance.

If it is desired to shift the equilibrium in the esterification of acetic acid with methanol (me) towards methyl acetate (me-ac), the latter must be distilled continuously from the reaction mixture. This however produces an azeotrope of 80% by weight of methyl acetate and 20% by weight of methanol, which must be separated into its components.

According to the invention, this is done by introducing this azeotrope into the column I at a point at which acid conditions prevail, and advantageously at a temperature at which all the methyl acetate, but not all the methanol, evaporates. This feed point is advantageously at about the middle of the column.

The alkanal is introduced at the same height (together with, or separately from, the azeotropic mixture) or lower; in the present case, the alkanal is advantageously acetaldehyde (ald). At about the level of the third quarter of the column, an aqueous acid ($H_2O/H^+$) is introduced, and this, as it passes to the column bottom, causes the methanol to bond to the acetaldehyde. Consequently, virtually methanol-free methyl acetate, together with a proportion of the acetaldehyde, passes into the upper column zone. The methyl acetate is separated off in a side stripper II and the acetaldehyde, obtained as the top product, is advantageously returned to the column.

In the lower zone of the column, the acetal or hemiacetal is again cleaved. The acetaldehyde passes upward and in part again bonds fresh methanol, whilst in the lower zone an aqueous acidic methanol solution is obtained. The methanol is distilled from the latter in a side stripper III, in a conventional manner, and the aqueous acid is in part returned to the upper zone of the column.

As will be seen, the aqueous acid and the acetaldehyde each form a closed circuit. Accordingly, these substances need only be replenished to the extent of any unavoidable slight losses.

The process proceeds similarly (this version not being shown in the FIGURE) if instead of acetaldehyde an alkanal which is higher-boiling than methyl acetate, for example n-butyraldehyde, is employed. In that case, the top product obtained is almost exclusively methyl acetate, whilst at the bottom an aqueous acidic solution containing methanol and butyraldehyde is obtained. It is merely necessary to distil the methanol from this mixture in a side stripper. The solution which remains can then be directly returned to the upper part of the column I.

In an advantageous embodiment of the process according to the invention, an acidic ion exchanger is used instead of the aqueous acid. The exchanger can be arranged as a fixed bed in the middle zone of the column. However, for technological reasons it is advantageous to bring the mixture of substances into contact with the ion exchanger outside the column I, by taking off a proportion of the mixture at one or more points, passing it over the ion exchanger and returning it to the column at the same height. If an ion exchanger is used, the circuit of aqueous acid is (effectively) replaced by a water circuit.

In the other cases conforming to the general definition, the separation process according to the invention is carried out in the same manner as that described for the case of separating methyl acetate from methanol.

The only precondition is that the liquid mixture in question should contain an aliphatic alcohol and a lower-boiling component and that the latter should not be separable from the alcohol by simple conventional fractionation. If a plurality of lower-boiling components and/or a plurality of higher-boiling components is present, the top product and bottom product are each multi-component mixtures, whose separation into their components is not a subject of the present invention and accordingly does not require further discussion here. The same is true where the starting mixture contains two or more different alcohols. Such a case may at times entail separating these alcohols from one another in subsequent process steps.

Apart from the fact that the separation process involves a chemical stage, namely the intermediate acetalization, the method is a purely physical one, ie. it is substantially independent of the substances involved. Accordingly, it is not necessary to recite individually all the mixtures of this type which arise, or may arise, in industry. In practice, the aliphatic alcohols are mostly $C_1$–$C_8$-alkanols or alcohols, in particular including methanol, ethanol, propanol, isopropanol, butanols, butenols and methylbutenols. These alcohols are obtained, in various chemical processes, for example esterification and etherification processes, and also in solution or extraction processes, as a mixture with esters, ethers, ketones, alkenes and alkanes, which, because of the closely similar boiling points, can only be fractionated at considerable expense, or cannot be separated at all by fractionation, because of azeotrope formation. The same is of course true in cases where it is not the other substances, but the alcohols, which are regarded as the impurities. The distillation auxiliary employed is advantageously an alkanal which volatilizes completely, or at least substantially, under the distillation conditions. Alkanals which are high-boiling in relation to the alcohol are less suitable because of their low vapor pressure and hence because of their low concentration in the middle zone of the column. The alkanals used are therefore in the main $C_2$–$C_5$-alkanals, and especially acetaldehyde, propionaldehyde and n-butyraldehyde. On the other hand, formaldehyde is of limited suitability, because of its tendency to polymerize.

The amount of alkanal is advantageously chosen to provide not less than 0.5 mole, but preferably from 0.8 to 3 moles, of alkanal per mole of alcohol for the acetalization in the middle zone of the column.

Suitable acids are primarily non-volatile or only slightly volatile strong mineral acids or sulfonic acids, for example sulfuric acid, phosphoric acid, nitric acid and p-toluenesulfonic acid. Advantageously, these acids are employed in the form of an 0.001–2% strength aqueous solution. The amount of this solution should advantageously be such that in the middle zone of the column from 0.5 to 4 liters of the aqueous acid are available per liter of alkanol.

Suitable ion exchangers are in particular crosslinked styrene polymers bearing sulfonic acid groups, for example those available under the trademarks ®Lewatit SPL 108 and 118 and ®Lewasorb.

The amount of water in the lower zone of the column is in general from 1 to 5 liters per liter of the alcohol present there. The above statements concerning the nature and amount of the mixtures employed and of the auxiliaries are guideline values, but by means of these, and by following the teaching according to the invention, the distillation conditions to be employed for a specific individual case can readily be determined.

The last remark also applies to the temperature profile in the column, the pressure, the technical parameters of the process, such as the design of the column and the number of theoretical plates, and the reflux ratio. A certain residence time, dependent on the rate of formation of the acetal, must be provided in the middle zone of the column. If this time is short, the middle zone can be designed as a packed column of from 1 to 30 theoretical plates, whilst if the time is longer, it is advisable to use bubble-cap trays or valve trays, since with these the residence time can be set to any desired value. In principle, one theoretical plate suffices for the lower zone of the column, in which virtually no fractionation takes place, but in general a lower zone with from 5 to 15 theoretical plates is preferred. The same remark applies to the upper zone of column I, and to the side strippers II and III.

EXAMPLE 1

Separation of a methyl acetate/methanol azeotrope

Per hour, an azeotropic mixture of 107 g of methyl acetate and 27 g of methanol, as well as 63 g of acetaldehyde, were introduced at the level of the 19th plate (counting from the bottom) into a packed column (metal fabric rings of 5 mm diameter) of 200 cm height and 4 cm internal diameter, which had 45 theoretical plates and was operated under atmospheric pressure. Per hour, 70 g of 1% strength by weight aqueous sulfuric acid were fed to the column at the level of the 30th plate.

Using a reflux ratio of about 8, there were obtained at the top of the column 63 g per hour of acetaldehyde. In a side stripper, 106 g of methyl acetate were obtained per hour. The acetaldehyde was fed to the column at the level of the 19th plate. The methyl acetate was virtually free from methanol. At the level of the 10th plate, an aqueous acidic methanol solution was taken off, and from this a mixture of 27 g of methanol and 1 g of methyl acetate was distilled, per hour, in a side stripper. In view of the object of the experiment, namely to obtain pure methyl acetate by esterifying acetic acid with methanol, the purity of the recovered methanol suffices, since, in practice, the methanol is returned to the esterification stage.

The aqueous acid obtained at the bottom of the main column was returned to the column at the level of the 30th plate.

EXAMPLE 2

Separation of an n-pentane/methanol mixture

Using the apparatus and procedure described in Example 1, 105 g per hour of a mixture of 84 g of n-pentane and 21 g of methanol were separated quantitatively, with the aid of 35 g of acetaldehyde and 80 g of aqueous sulfuric acid, into its components.

EXAMPLE 3

Separation of a methyl acetate/methanol azeotrope

Using the apparatus and method described in Example 1, 149 g per hour of an azeotropic mixture of 119 g of methyl acetate and 30 g of methanol were separated, with the aid of 50 g of propionaldehyde and 55 g of aqueous sulfuric acid, into a top fraction consisting of 118 g of methyl acetate and 50 g of propionaldehyde and a bottom fraction consisting of the aqueous acid, 29.5 g of methanol and about 1 g of methyl acetate. The top fraction was separated, by simple fractionation in a separate column, into propionaldehyde and methyl acetate which still contained some methanol.

The methanol was subsequently separated from the bottom fraction in a side stripper.

EXAMPLE 4

Separation of a methyl acetate/ethanol mixture

Using the apparatus and method described in Example 1, 139 g per hour of a mixture of 127 g of methyl acetate and 12 g of ethanol were separated quantitatively into its components with the aid of 21 g of acetaldehyde and 80 g of aqueous sulfuric acid, at a reflux ratio of 3.

EXAMPLE 5

Separation of a methyl acetate/methanol mixture

Using the apparatus described in Example 1, but without the two side strippers, 112 g per hour of a mixture of 75 g of methyl acetate and 37 g of methanol were separated, with the aid of 37 g of n-butyraldehyde and 80 g of aqueous sulfuric acid, into a top fraction of 72 g/h of methyl acetate, 2.5 g/h of water and 0.5 g/h of methanol, and a bottom fraction of aqueous acid, methanol, butyraldehyde, a small amount of butyraldehyde-dimethylacetal and a small amount of methyl acetate. The reflux ratio was about 4.

We claim:

1. A process for the distillative separation in a fractionating column of a liquid mixture containing at least one aliphatic alcohol into a higher-boiling alcohol-containing fraction and a lower-boiling fraction of the other liquids, which process comprises:
    contacting the alcohol in a middle zone of the column with a $C_2$- to $C_5$-alkanal and with a non-volatile or only slightly volatile acid;
    maintaining said middle zone of the column under conditions of temperature and pressure sufficient to cause a transient bonding of the alcohol to the alkanal in the presence of said acid so as to form a higher boiling acetal or hemiacetal;
    heating the column such that substances more volatile than the alcohol pass into the upper zone of the column for removal therefrom as a top product;
    cleaving said acetal or hemiacetal in the lower zone of the column into its respective alcohol and alkanal components; and
    separating the alcohol from the bottom product of the column.

2. A process as claimed in claim 1, wherein
    (a) the alcohol-containing starting mixture is introduced into the middle zone of the column at a temperature at which the lower-boiling fraction vaporizes completely but the higher-boiling fraction does not,
    (b) an alkanal which is higher-boiling than the alcohol is introduced into the upper zone of the column,
    (c) an aqueous solution of the acid is introduced into the upper quarter of the column,
    (d) the lower-boiling fraction is taken off at the top and is fractionated in a conventional manner, where appropriate with the aid of side strippers and
    (e) the alcohol- and alkanal-containing aqueous acidic fraction which forms in the lower zone of the column is taken off from there and is fractionated, in a side stripper, to give an alcohol-containing fraction and a mixture of aqueous acid and alkanal, and the last-mentioned mixture is returned to the upper zone of the column.

3. A process as claimed in claim 1 including the steps of
    contacting liquid from said middle zone of the column with an acidic ion exchanger as a non-volatile acid, and
    conducting water from the ion exchanger to the lower zone of the column.

4. A process as claimed in claim 1, wherein
    (a) the alcohol-containing starting mixture is introduced into the middle zone of the column at a temperature at which the lower-boiling fraction vaporizes completely but the higher-boiling fraction does not,
    (b) a $C_2$- to $C_5$-alkanal which is lower-boiling than the alcohol is introduced into the middle or lower zone of the column,
    (c) an aqueous solution of the acid is introduced into the upper quarter of the column,
    (d) the lower-boiling fraction is taken off at the top, and the alkanal which passes, together with the lower-boiling fraction, into the upper zone of the column is separated off and returned to the middle zone of the column, and
    (e) the alcohol-containing aqueous fraction which forms in the lower zone of the column is taken off from there and is separated, in a side stripper, into the alcohol or an alcohol-containing fraction, and an aqueous fraction, and the last-mentioned fraction is returned to the upper zone of the column.

5. A process as claimed in claim 4 wherein said lower-boiling fraction consisting of a plurality of components is fractionated in the upper zone of the column.

6. A process as claimed in claims 1, 4, 2, 3 or 5 wherein said alkanal is selected from the group consisting of acetaldehyde, propionaldehyde and n-butyraldehyde.

* * * * *